United States Patent
Asinovsky

[11] Patent Number: 5,803,085
[45] Date of Patent: Sep. 8, 1998

[54] NON-ELASTIC CONDOM

[76] Inventor: Vladimir A. Asinovsky, 12322 Ella Lee La., Houston, Tex. 77077

[21] Appl. No.: 661,645

[22] Filed: Jun. 11, 1996

[51] Int. Cl.$^6$ ........................................ A61F 6/04
[52] U.S. Cl. .......................... 128/844; 128/918
[58] Field of Search ..................... 128/842, 844, 128/918; 604/347–353

[56] References Cited

U.S. PATENT DOCUMENTS

| | | | |
|---|---|---|---|
| 2,138,626 | 6/1938 | Copen | 2/21 |
| 2,670,736 | 3/1954 | Dunkelberger | 128/844 |
| 3,648,700 | 3/1972 | Warner | 128/294 |
| 4,432,357 | 2/1984 | Pomeranz | 128/79 |
| 4,685,913 | 8/1987 | Austin | 604/353 |
| 4,817,593 | 4/1989 | Taller | 128/844 |
| 5,121,755 | 6/1992 | Hegedusch | 128/844 |
| 5,158,556 | 10/1992 | Starley | 604/351 |
| 5,207,233 | 5/1993 | Barnes | 128/842 |
| 5,327,911 | 7/1994 | Pien | 128/844 |
| 5,361,779 | 11/1994 | Wilson | 128/844 |
| 5,370,131 | 12/1994 | Hess | 128/844 |
| 5,391,343 | 2/1995 | Dreibelbis et al. | 264/216 |
| 5,399,400 | 3/1995 | Nile et al. | 428/36.8 |
| 5,454,379 | 10/1995 | Shephard | 128/842 |

FOREIGN PATENT DOCUMENTS 1250553  10/1971  United Kingdom ................... 128/844

*Primary Examiner*—Michael A. Brown
*Attorney, Agent, or Firm*—Joseph N. Breaux

[57] ABSTRACT

A non-elastic condom comprising a sheath member having an insertion opening in connection with a penis receiving compartment formed therein that is sized to loosely cover the glans and body portion of a penis. The sheath member is cast, skived or otherwise conventionally formed from a polytetrafluoroethylene (PTFE) polymer. A securing mechanism, such as a two ended tether or heat resistant elastic band, is provided adjacent the insertion opening to secure the sheath securely about the body portion of the penis to maintain the sheath over the penis in use.

9 Claims, 2 Drawing Sheets

NON-ELASTIC CONDOM

TECHNICAL FIELD

The present invention relates to devices for shielding the male penis during sexual intercourse and more particularly to a non-elastic, chemically inert, loose-fitting, low friction condom for shielding the male penis during sexual intercourse.

BACKGROUND ART

Conventional condoms provide a physical barrier to the transmission of disease-producing viruses between sexual partners and serve contraceptive purposes. The conventional condom is a thin elastomeric membrane that is rolled over and tightly covers the penis. Although conventional condoms are effective for minimizing transmission of disease producing viruses and for contraceptive purposes, the thin membrane tightly covering the penis eliminates the tactile lateral frictional sensation produced in the skin receptors of the penis surface that is present during sexual intercourse without a tight fitting elastic condom. It would be a benefit, therefore, to have a condom that could provide a barrier for preventing the transmission of diseases and for providing a contraceptive effect that did not eliminate said frictional sensation in the skin receptors of the penis during sexual intercourse.

In addition, because conventional condoms are constructed from an elastic material such as latex, it is necessary to utilize a lubricant with the condom to reduce adhesion of the condom to the sexual partner. It is important to avoid oil based lubricants with conventional condoms because the oil in the lubricant can rapidly degrade the latex forming the condom causing the condom to disintegrate or to break. It would be a benefit, therefore, to have a condom constructed from a material that can be used in conjunction with oil based lubricants. It would be a further benefit to have a condom constructed from a material having a low coefficient of friction to minimize the need for lubricants.

Additionally, because conventional condoms are exposed to bodily fluids during use, they must be disposed of as biological waste. It would be a benefit, therefore, to have a condom that could be sterilized prior to disposal or sterilized and reused a number of times prior to discarding. Of course, it would also be a benefit if the non-elastic condom could be chemically sterilized by immersion in a commonly available cleaning and disinfecting solution, such as alcohol, or heat sterilized by immersion in boiling or heated water. The availability of a condom that can be sterilized and reused would be a benefit to individuals on low incomes.

GENERAL SUMMARY DISCUSSION OF INVENTION

It is thus an object of the invention to provide a non-elastic condom that provides a physical barrier for contraception and the prevention of disease transmission.

It is a further object of the invention to provide a non-elastic condom that includes a non-elastic membrane adapted for covering the penis that does not diminish the lateral frictional sensation to the penis during sexual intercourse.

It is a still further object of the invention to provide a non-elastic condom that is constructed from a material having a low coefficient of friction to minimize the need for lubricants during sexual activity.

It is a further object of the invention to provide a non-elastic condom that is constructed from a material that can be used in conjunction with oil-based lubricants.

It is a still further object of the invention to provide a non-elastic condom that can be disinfected with commonly available disinfectant solutions.

It is a still further object of the invention to provide a non-elastic condom that can be heat disinfected.

It is a still further object of the invention to provide a non-elastic condom that accomplishes all or some of the above objects in combination.

Accordingly, non-elastic condom is provided. The non-elastic condom of the present invention comprises a non-porous sheath member having an insertion opening in connection with a penis receiving compartment formed therein that is sized to loosely cover the glans and body portion of a penis. The sheath member is cast, skived or otherwise conventionally formed from a polytetrafluoroethylene (PTFE) polymer. A securing mechanism is provided adjacent the insertion opening to secure the sheath securely about the body portion of the penis to maintain the sheath over the penis in use. The securing mechanism preferably includes a constriction mechanism, such as a two ended tether or heat-resistant resilient band, to constrict the insertion opening end of the sheath member about the body of the penis without adversely affecting the function of the penis during sexual intercourse.

Because PTFE polymers are chemically inert, use of a sheath member formed of PTFE polymers allows the use of a variety of lubricants, cleaning and disinfecting solutions in conjunction with the sheath member when desired. Because PTFE is resistant to temperatures well above the boiling point of water, the sheath member can also be thermally cleaned and disinfected in boiling water to clean and disinfect it prior to disposal or reuse.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

EXEMPLARY MODE FOR CARRYING OUT THE INVENTION

Figure 1:
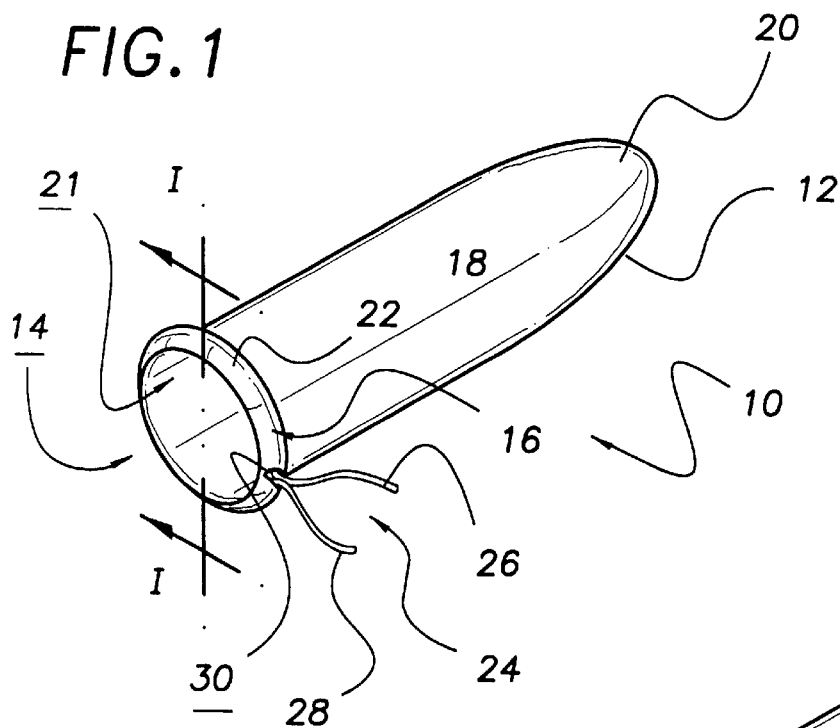
FIG. 1 is a perspective view of a first exemplary embodiment of the non-elastic condom of the present invention showing the sheath member including the insertion opening and the penis insertion compartment, and a first preferred securing mechanism including a containment channel with the first and second ends of the securing tether extending from a tether aperture formed through the side of the containment channel.

FIG. 1 shows a first exemplary embodiment of the non-elastic condom of the present invention generally designated by the numeral 10. Condom 10 includes a sheath member 12 having an insertion opening 14, and a securing mechanism for securing the insertion opening about the penis, generally designated by the numeral 16. Sheath member 12 is cast from polytetrafluoroethylene (PTFE) and has a nominal thickness of 0.6 mils. Sheath member 12 has a tubular portion 18 extending between insertion opening 14 and a contoured tip section 20. Tubular portion 18 and contoured tip section 20 define a penis receiving compartment 21. In this embodiment, tubular portion 18 has a diameter of two inches and a length of eight inches. Of course, these dimensions are only exemplary. The criteria for selecting the length and diameter is to select the length and diameter of tubular section 18 to provide a loose fitting covering for the glans and a portion of the body of the penis in use. The loose fit is necessary in order to not diminish the lateral frictional sensation to the pressure receptors along the body of the penis during sexual intercourse.

Figure 2:
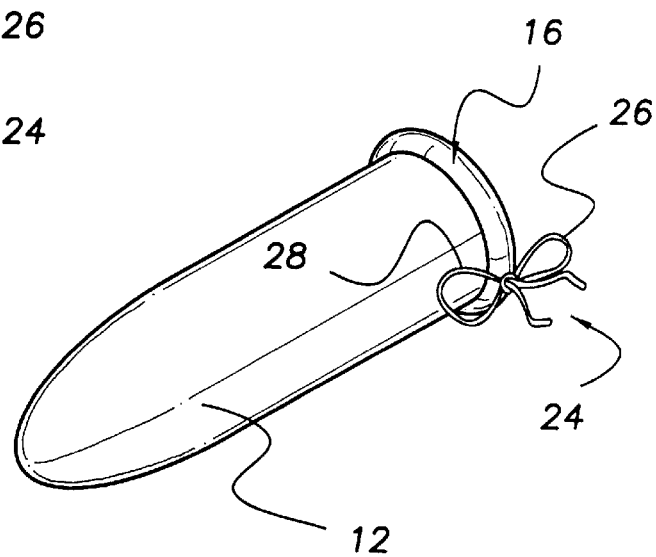
FIG. 2 is a perspective view of the non-elastic condom of FIG. 1 showing the first and second ends of the securing tether tied in a bow as in use.
Figure 3:
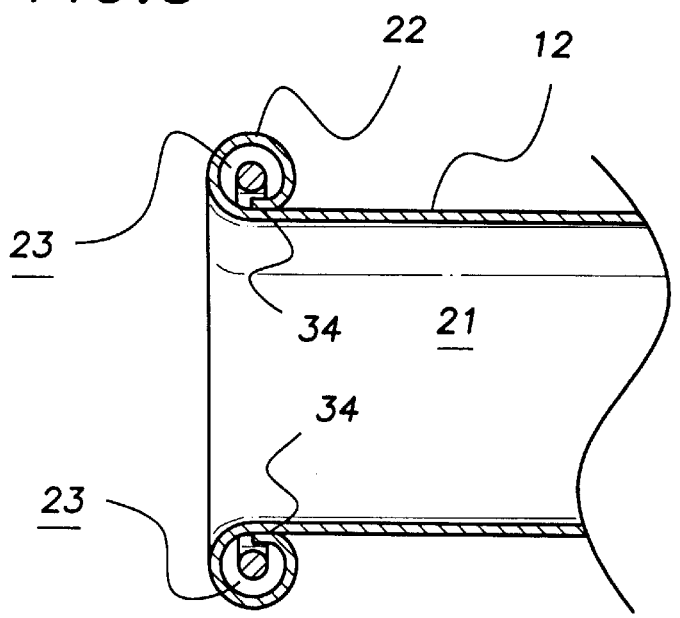
FIG. 3 is a cross sectional view of the first exemplary embodiment along the line I—I of FIG. 1 showing a first preferred configuration for forming the containment channel.

In this embodiment securing mechanism 16 includes a containment channel 22 formed adjacent to insertion opening 14 that defines a passageway 23 (shown in FIG. 3) around the perimeter of insertion opening 14. A two ended tether, generally designated 24, is threaded through the passageway and both ends 26,28 extend out from a tether aperture 30 formed through the sidewall of containment channel 22. FIG. 2 shows ends 26,28 of two ended tether 24 tied into a bow. In use, securing mechanism 16 is used to constrict insertion opening 14 about the body of the penis and maintain sheath member 12 on the penis by tightening two ended tether 24 and then tying ends 26,28 in a knot or bow. FIG. 3 shows one method of forming containment channel 22 by rolling the edge 34 of sheath member 12 to form a tubular passageway and the securing edge 34 between containment channel 22 and the exterior of sheath 12. Edge 34 may be secured with a suitable adhesive, by the application of sufficient heat, or any other method known in the art.

Figure 4:
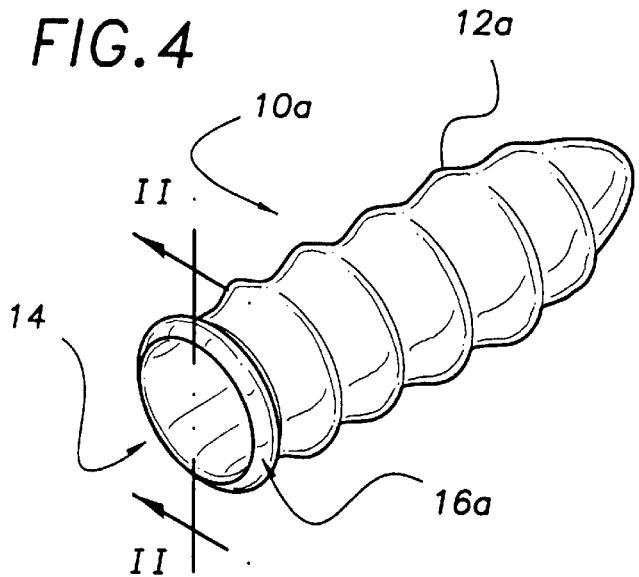
FIG. 4 is a perspective view of a second exemplary embodiment of the non-elastic condom of the present invention showing a second exemplary sheath member including the insertion opening and the penis insertion compartment, and a second preferred securing mechanism including a containment channel having an elastic band trapped therein.
Figure 5:
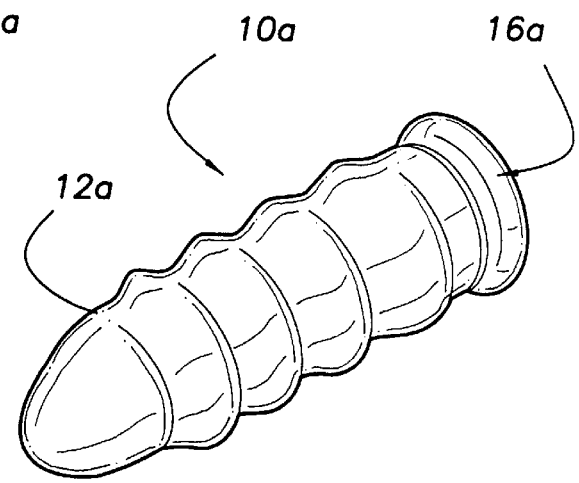
FIG. 5 is a second perspective view of the non-elastic condom of FIG. 4.
Figure 6:
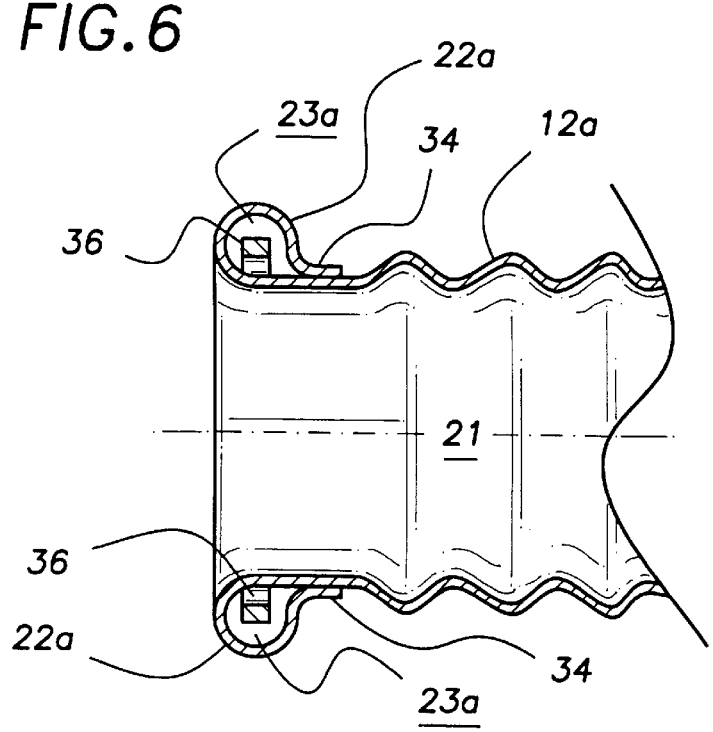
FIG. 6 is a cross sectional view of the second exemplary embodiment along the line II—II of FIG. 4 showing a second preferred configuration for forming the containment channel.

FIGS. 4 and 5 show a second exemplary embodiment of the non-elastic condom of the present invention generally designated by the numeral 10a. Condom 10a includes a sheath member 12a that is identical to that of condom 10 except sheath member 12a is constructed to have a varying diameter penis receiving compartment 21 and a securing mechanism 16a that includes a heat resistant restriction band 36 (shown in FIG. 6) housed within a containment channel 22a formed adjacent to insertion opening 14. With reference to FIG. 6, in this embodiment containment channel 22a is formed by rolling the edge 34 of sheath member 12a to form a tubular passageway 23a and then securing the edge to the exterior of sheath 12a in a manner such that containment channel 22a is adjacent to edge 34. In this embodiment restriction band 26 is formed from neoprene rubber, however, any resilient material that can withstand immersion in boiling water for at least one minute is suitable.

Use of condom 10,10a is now described with general reference to FIGS. 1–6. Condom 10,10a is placed over the penis prior to sexual intercourse and secured with securing mechanism 16,16a as previously described. After intercourse is complete, condom 10,10a is removed and disinfected by immersion in a disinfecting solution or boiling water prior to disposal or reuse.

It can be seen from the preceding description that a non-elastic condom has been provided that provides a physical barrier for contraception and the prevention of disease transmission; that includes a non-elastic membrane adapted for covering the penis that does not diminish the lateral frictional sensation to the penis during sexual intercourse; that is constructed from a material having a low coefficient of friction to minimize the need for lubricants during sexual activity; that is constructed from a material that can be used in conjunction with oil-based lubricants; that can be disinfected with commonly available disinfectant solutions; and that can be heat disinfected.

It is noted that the embodiment of the non-elastic condom described herein in detail for exemplary purposes is of course subject to many different variations in structure, design, application and methodology. In particular the securing mechanism is subject to a range of variations and it is contemplated that it can take various forms conventionally known in the art. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A non-elastic condom comprising:

a non-porous sheath member providing a non-elastic membrane formed from a polytetra-fluoroethylene (PTFE) polymer, said sheath member having an insertion opening in connection with a penis receiving compartment formed therein that is shaped to loosely cover the glans and body portion of a penis; and a securing mechanism in connection with said sheath member for securing the sheath about the body portion of the penis during use.

2. The non-elastic condom of claim 1, wherein:

said securing mechanism includes a constricting mechanism housed within a channel formed adjacent to said insertion opening.

3. The non-elastic condom of claim 2, wherein:

said channel is formed from a rolled edge of said sheath member.

4. The non-elastic condom of claim 2 wherein:

said constricting mechanism is a tether.

5. The non-elastic condom of claim 3 wherein:

said constricting mechanism is a tether.

6. The non-elastic condom of claim 2 wherein:

said constricting mechanism is a resilient band.

7. The non-elastic condom of claim 3 wherein:

said constricting mechanism is a resilient band.

8. The non-elastic condom of claim 1 wherein:

said sheath member has a varying diameter penis receiving compartment.

9. A non-elastic condom comprising:

a non-porous sheath member providing a non-elastic membrane formed entirely from a polytetra-fluoroethylene (PTFE) polymer, said sheath member having an insertion opening in connection with a penis receiving compartment formed therein that is shaped to loosely cover the glans and body portion of a penis; and a securing mechanism in connection with said sheath member for securing the sheath about the body portion of the penis during use.

* * * * *